United States Patent
Kuo et al.

(10) Patent No.: US 8,168,648 B2
(45) Date of Patent: May 1, 2012

(54) CAMPTOTHECIN DERIVATIVES AND USES THEREOF

(75) Inventors: Min-Wen Kuo, Taipei (TW); Yung-Hsu Chan, Taipei (TW); Yun-Long Tseng, Taipei (TW); Siong-Tern Liew, San Francisco, CA (US); Keelung Hong, San Francisco, CA (US)

(73) Assignees: Taiwan Liposome Co., Ltd., Taipei (TW); TLC Biopharmaceuticals, Inc., San Francisco, CA (US)

( * ) Notice: Subject to any disclaimer, the term of this patent is extended or adjusted under 35 U.S.C. 154(b) by 250 days.

(21) Appl. No.: 12/718,764

(22) Filed: Mar. 5, 2010

(65) Prior Publication Data

US 2010/0227877 A1 Sep. 9, 2010

Related U.S. Application Data

(60) Provisional application No. 61/158,125, filed on Mar. 6, 2009.

(51) Int. Cl.
*A61K 31/4745* (2006.01)
*C07D 491/22* (2006.01)

(52) U.S. Cl. .......................... 514/283; 546/48
(58) Field of Classification Search ............. 514/283; 546/48

See application file for complete search history.

(56) References Cited

U.S. PATENT DOCUMENTS 7,875,602 B2 * 1/2011 Yang ........................ 514/183

FOREIGN PATENT DOCUMENTS

WO    PCT/US95/08786    2/1996

OTHER PUBLICATIONS

U.S. Appl. No. 11/444,150, filed Oct. 13, 2005, Hossner.

* cited by examiner

*Primary Examiner* — Charanjit Aulakh
(74) *Attorney, Agent, or Firm* — Occhiuti Rohlicek & Tsao LLP

(57) ABSTRACT

The present invention provides two new camptothecin derivatives, which were identified as S,R- and S,S-topotecan lactates, respectively. Both compounds have anticancer activities. Pharmaceutical compositions of the new camptothecin derivatives, and cancer therapies with the new camptothecin derivatives or their pharmaceutical compositions were also provided.

6 Claims, No Drawings

CAMPTOTHECIN DERIVATIVES AND USES THEREOF

RELATED APPLICATION

This application claims priority to U.S. Provisional Application No. 61/158,125, filed on Mar. 6, 2009, the content of which is hereby incorporated by reference in its entirety.

TECHNOLOGY FIELD

The present invention relates to novel camptothecin derivatives and uses thereof.

BACKGROUND OF THE INVENTION

Cancer is the second leading cause of death in the United States and accounts for the deaths of one of every four Americans. According to the American Cancer Society, 7.6 million people worldwide died of cancer in 2007.

Camptothecin is a well known anticancer drug isolated from the Chinese native tree *Camptotheca acuminate*. It is an optically active (20S) alkaloid of the fused ring system shown below.

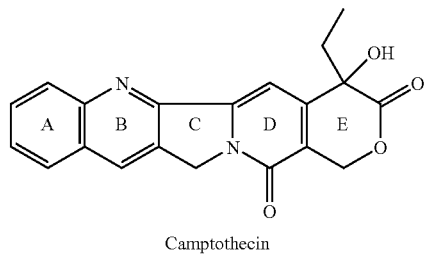

Camptothecin

Many efforts have been directed to synthesizing camptothecin derivatives to modify the cytotoxicity activity and/or improve water-solubility. Patent Corporation Treaty (PCT) International Application No. PCT/US95/08786 (WO 96/02546) discloses water-soluble esters of camptothecin compounds wherein the E-ring of the camptothecin esters has one of the structures shown below where m, $R^9$, $R^{10}$ and $R^{11}$ have the definitions as given:

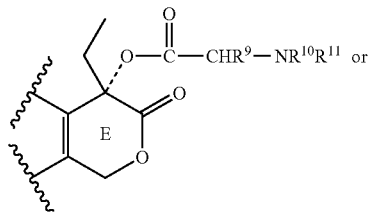

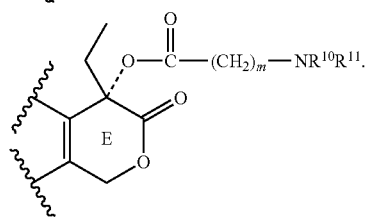

In addition, U.S. patent application Ser. No. 11/444,150 (U.S. 20070093432) discloses camptothecin-based compounds modified by positing at least one electron-affinic group around the camptothecin structure to enhance their value in combination with radiotherapy. Other camptothecin derivatives include, for example, topotecan, which is of the structure shown below.

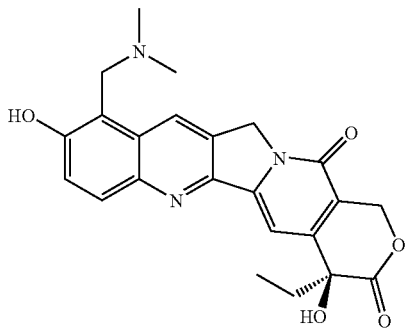

topotecan

A need continues to exist for new camptothecin derivatives with anticancer activities.

BRIEF SUMMARY OF THE INVENTION

This present invention is based on the discovery that a known camptothecin derivative named TLC388 (see below) is modified in vivo after administration and the modified camptothecin derivatives exhibit anticancer activities.

It is therefore an aspect of the invention to provide a new compound which is represented by Formula I

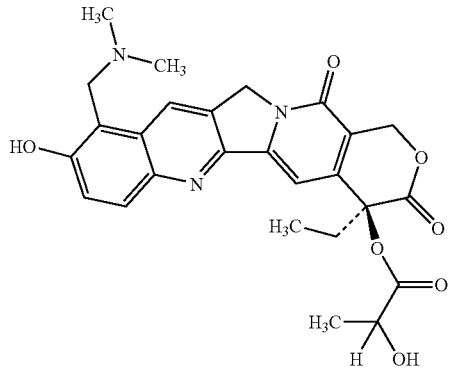

Formula I or a pharmaceutically acceptable salt thereof.

In one embodiment, the compound of the invention is of Formula II

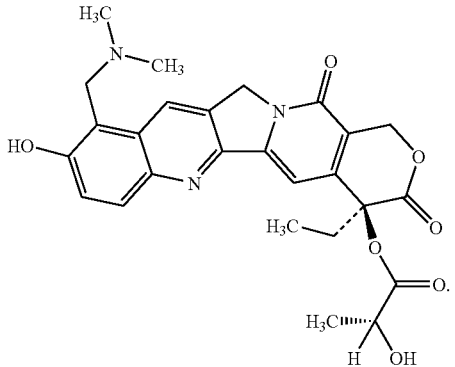

Formula II

In another embodiment, the compound of the invention is of Formula III

Formula III

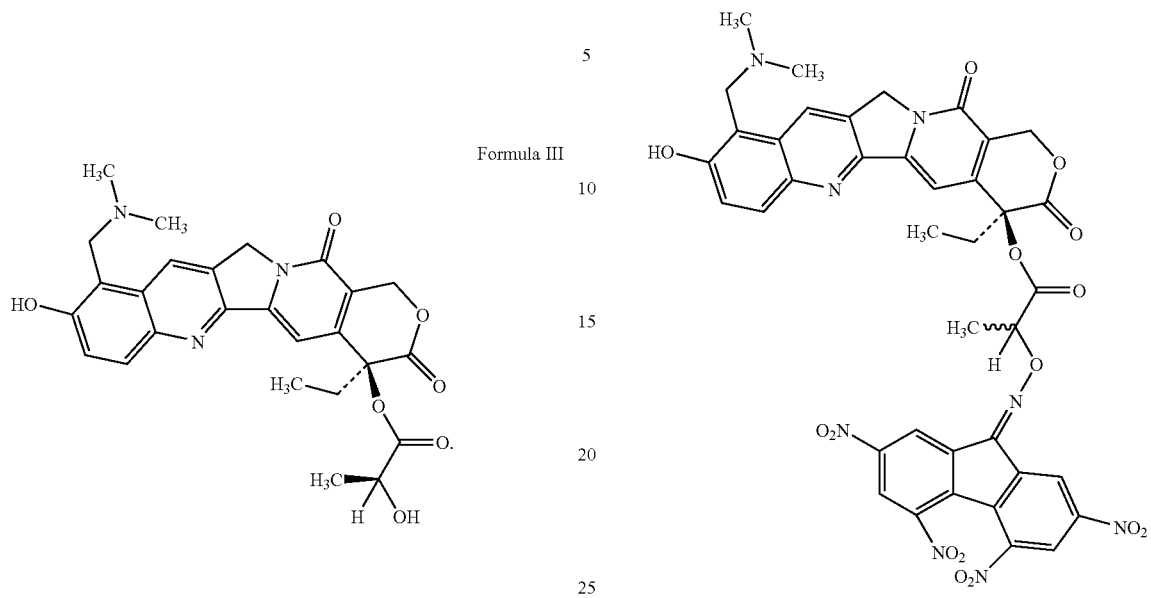

TLC388

It is another aspect of the invention to provide a pharmaceutical composition comprising at least one of the compounds as described above or a pharmaceutically acceptable salt thereof together with a pharmaceutically acceptable carrier.

It is yet another aspect of the invention to provide a method for treating a cancer in a subject in need thereof comprising administrating to the subject at least one of the compounds as described above, a pharmaceutically acceptable salt thereof, or the above-mentioned pharmaceutical composition.

The details of one or more embodiments of the invention are set forth in the description below. Other features or advantages of the present invention will be apparent from the following detailed description of several embodiments, and also from the appending claims.

DETAILED DESCRIPTION OF THE INVENTION

Unless defined otherwise, all technical and scientific terms used herein have the same meanings as is commonly understood by one of skill in the art to which this invention belongs.

As used herein, the articles "a" and "an" refer to one or more than one (i.e., at least one) of the grammatical object of the article. By way of example, "an element" means one element or more than one element.

TLC388 of the following structure is one of the camptothecin derivatives disclosed in the above-mentioned U.S. application Ser. No. 11/444,150 as chemoradiosensitizing agents for cancer therapy.

In the present study, we conducted an in vivo study for TLC388 in Sprague-Dawley rats and isolated two metabolites thereof from the biological samples of the rats. The two metabolites were subsequently confirmed to have the same chemical structure (i.e. topotecan lactate) but different steric configurations, one being S,R-topotecan lactate (U1) and the other being S,S-topotecan lactate (U2). Both of the metabolites exhibit anticancer activities.

Accordingly, in one aspect, the present invention provides a compound (topotecan lactate) which is represented by Formula I Formula I or a pharmaceutically acceptable salt thereof.

In one embodiment, the compound of the invention is S,R-topotecan lactate which is represented by Formula II Formula II

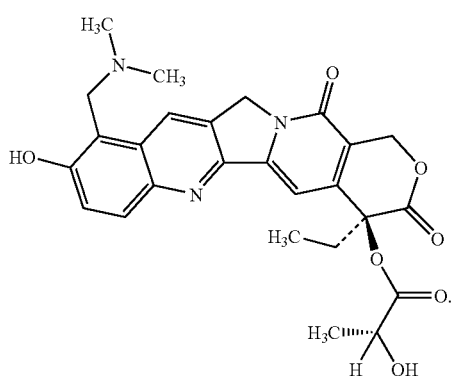

In another embodiment, the compound of the invention is S,S-topotecan lactate which is represented by Formula III Formula III

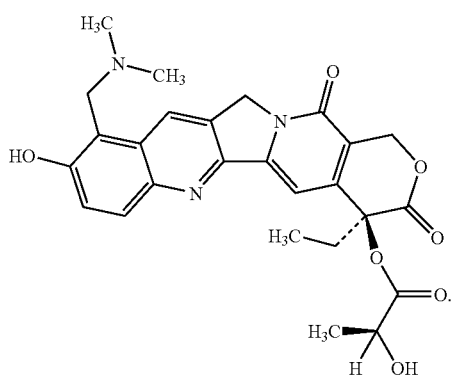

As used herein, the term "S" or "R" is a way to name an optical isomer by its configuration, without involving a reference molecule, which is called the R/S system. It labels each chiral center R or S according to a system by which its ligands are each assigned a priority, according to the Cahn Ingold Prelog priority rules, based on atomic number. This system labels each chiral center in a molecule (and also has an extension to chiral molecules not involving chiral centers). If the compound has two chiral centers, it can be labeled, for example, as an (S,S) isomer versus an (S,R) isomer.

As used herein, the term "pharmaceutically acceptable salt" includes acid addition salts. "Pharmaceutically acceptable acid addition salts" refer to those salts which retain the biological effectiveness and properties of the free bases, which are formed with inorganic acids such as hydrochloric acid, hydrobromic acid, sulfuric acid, nitric acid, phosphoric acid and the like, and organic acids such as acetic acid, propionic acid, pyruvic acid, maleic acid, malonic acid, succinic acid, fumaric acid, tartaric acid, citric acid, benzoic acid, mandelic acid, methanesulfonic acid, ethanesulfonic acid, p-toluenesulfonic acid, salicylic acid, trifluoroacetic acid and the like.

The compounds of the invention have been demonstrated to have inhibitory effects on growth of various cancer cells. Due to the anti-cancer activity, the compounds of the invention are useful in the treatment of a cancer in a subject in need thereof.

Accordingly, the present invention relates to a method for treating a cancer in a subject in need thereof comprising administrating to the subject at least one of the compounds as described herein.

As used herein, the term "cancer" is to be considered in the broadest general definition as a malignant neoplasm, an abnormal mass of tissue, the growth of which exceeds and is uncoordinated with that of normal tissues and persists in the same excessive manner after cessation of the stimuli that evoked the change. Examples of the types of cancers that may be treated by the compounds of the invention includes, but are not limited to, colon cancer, breast cancer, small cell lung cancer and non-small cell lung cancer, which are shown in Table 4 of Example 5 below.

As used herein, a subject in need of the treatment according to the invention includes human and non-human mammals. Non-human mammals include, but are not limited to, companion animals such as cats, dogs and the like and farm animals such as cattle, horses, sheep, goats, swine and the like.

As used herein, the term "anti-cancer effect" refers to inhibiting or retarding the growth of malignant cells, or in the case of a subject having a malignant tumor, the rate of tumor growth is decreased, the volume of such tumor is reduced, or the tumor is eliminated entirely.

The compounds of the invention may be administered by a medically acceptable route such as orally, parentally (e.g. intramuscularly, intravenously, subcutaneously, interperitoneally), transdermally, rectally, by inhalation and the like.

In addition, the compounds of the invention are preferably formulated with a pharmaceutically acceptable carrier to form a pharmaceutical composition for use in the above mentioned treatments. Accordingly, the present invention further relates to a pharmaceutical composition comprising at least one of the compounds as described above or a pharmaceutically acceptable salt thereof together with a pharmaceutically acceptable carrier.

As used herein, the term "pharmaceutical composition" refers to a composition suitable for a pharmaceutical use in a subject. A pharmaceutical composition comprises a pharmacologically effective amount of an active agent and a pharmaceutically acceptable carrier. "Pharmacologically effective amount" refers to that amount of an agent effective to produce the intended pharmacological result. "Pharmaceutically acceptable carrier" refers to any of the standard pharmaceutical carriers. Such carriers may include, but are not limited to, saline, buffered saline, dextrose, water, glycerol, ethanol and combinations thereof.

The pharmaceutical composition of the present invention can be manufactured by conventionally known methods with one or more pharmaceutically acceptable carriers. In addition, the pharmaceutical composition of the present invention may be constituted into any forms suitable for the mode of administration selected. For example, compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

In addition to standard carriers, an oral pharmaceutical composition of the present invention may be supplemented with one or more excipient that are normally employed in oral formulations, such as surfactants, solubilizers, stabilizers, emulsifiers, thickeners, coloring agents, sweetening agents, flavoring agents, and preservatives. Such excipients are well known to those skilled in the art.

The dosage of the pharmaceutical composition or the compound of the present invention can be determined by the skilled person in the art according to the embodiments. Unit doses or multiple dose forms are contemplated, each offering advantages in certain clinical settings. According to the present invention, the actual amount of the compound or pharmaceutical composition to be administered can vary in accordance with the age, size, and condition of the subject to be treated, depending on the discretion of medical professionals.

The present invention is further illustrated by the following examples, which are provided for the purpose of demonstration rather than limitation.

EXAMPLE 1

Isolation of Compounds

1. In Vivo Study of TLC388 in Rats

Two male Sprague-Dawley (SD) rats (about 250 g, Bio-LASCO Taiwan Co., Ltd.) were provided and acclimated inside TLC animal room for at least 7 days before the experiment. TLC388, prepared as described in U.S. patent application Ser. No. 11/444,150, the entity of which is incorporated herein by reference, was reconstituted by WFI (water for injection) and then IV-bolus administered to the rats in an amount of 80 mg/kg based on the weight of the rats. At different time point, rat bloods were collected from jugular vein and stabilized with anticoagulants (sodium fluoride/potassium oxalate) and citrate acid (2 mg/mL blood). After centrifugation (750×g, 4° C., 5 min), plasma was collected and then treated with four volumes of acidic methanol (20 mM perchloric acid) to precipitate protein. After centrifugation (20000×g, 4° C., 30 min), the supernatants were directly used for HPLC analysis.

2. HPLC Analysis

The collected supernatants as described above were injected into a high-pressure liquid chromatogram (HPLC) system. The HPLC system used herein was a Waters HPLC system (Alliance® 2695) with a Phenomenex® Gemini® RP18 column (4.6×250 mm, 5 μm, 110 Å, thermostated at 35° C.) as an analytical column and a fluorescence detector (Waters 2475) for detection. The mobile phase consisted of a mixture of MeOH and 50 mM phosphate buffer with ammonium hydroxide (pH 4.0±0.5). Table 1 shows the elution program.

TABLE 1

HPLC elution program

| Time | % Buffer | % MeOH | Flow rate (mL/min) |
| --- | --- | --- | --- |
| 0.01 | 80 | 20 | 1 |
| 8 | 35 | 65 | 1 |
| 20 | 35 | 65 | 1 |
| 21 | 0 | 100 | 1 |
| 22 | 0 | 100 | 1 |
| 23 | 80 | 20 | 1 |
| 28 | 80 | 20 | 1 |

The samples eluted from the analytical column were forced to react with a reaction solution (75 mM NaOHaq, flow rate: 0.5 mL/min) and detected by the fluorescence detector (Ex 404 nm/Em 516 nm). Table 2 shows the retention time of detected products.

TABLE 2

Retention time of detected products.

| Products | Retention time (min) |
| --- | --- |
| S,S-TLC388 | 17.1 |
| S,R-TLC388 | 18.4 |
| topotecan | 8.0 |
| unknown 1 ("U1") | 8.6 |
| unknown 2 ("U2") | 8.9 |

As shown in Table 2, two diastereomers of TLC388 (S,S-TLC388 and S,R-TLC388), topotecan and two unknown compounds (U1 and U2) were detected in the HPLC elution. We found that the two unknown compounds appeared in the blood/plasma immediately after the administration of TLC388; they continue to be observed for at least 2 hours and considered to be relatively abundant within 30 minutes. We also found that the two unknown compounds appeared close to topotecan. We therefore suggested that these unknown compounds were topotecan related compounds, and conducted subsequent experiments to identify their structures.

EXAMPLE 2

Preliminary Identification of Compounds

1. Fluorescence Spectra Analysis

A Waters fluorescence detector (Waters 2475) coupled to a Waters HPLC separation module (Waters 2695) was used for acquiring fluorescence spectra of the compounds detected during the HPLC analyses. According to the fluorescence spectra obtained (data not shown), topotecan exhibited maximum fluorescence emission and excitation peaks at 510.0 nm and 367.5 nm, respectively, and U1 and U2 showed similar fluorescence spectra profiles thereto. We therefore suggested that U1 and U2 shared the same chromophore as that of topotecan.

2. Mass Spectra Analysis

A mass analyzer (Bruker®, Esquire2000) coupled to a HPLC separation system (Agilent®, 1100 series) was used for acquiring mass spectra of the compounds detected during the HPLC analyses. The HPLC separation system was equipped with a reverse phase analytical column (Phenomenex® Gemini 5 μm RP18 column, 4.6×250 mm). The interface between the HPLC separation system and the mass analyzer was electrospray ionization (ESI), which was used to ionize the analytes. The mobile phase for separating the compounds was essentially the same as in Table 1, except that it was run under isocratic condition with 30:70 volume ratio (buffer vs. methanol).

According to the mass spectra obtained from the LC-MS/MS analysis (data not shown), topotecan gave a molecular ion at m/z 422 amu and daughter ions at m/z 377 amu and 342 amu. In the same run, U1 gave a molecular ion at m/z 494 amu and daughter ions at m/z 449 amu and 359 amu. U2 exhibited the same MS spectra as U1. We therefore suggested that U1 and U2 shared the same chemical structure but different steric configuration. They were supposed to be S,R-topotecan lactate (U1) and S,S-topotecan lactate (U2), respectively.

EXAMPLE 3

Synthesis of Compounds

To confirm the chemical structures of U1 and U2, S,R-topotecan lactate and S,S-topotecan lactate were respectively synthesized and purified for use in the subsequent HPLC comparison analysis (see Example 4 below).

1. General Methods $^1$H and $^{13}$C spectra were recorded on a Varian Unity Inova NMR Spectrometer operating at 400 and 100 MHz, respectively. Chemical shifts were referenced to the solvent used (7.27 and 77.23 ppm for CDCl$_3$, 3.31 and 49.15 ppm for CD3OD) unless otherwise stated. Electrospray-ionization mass spectra (ESIMS) were acquired using a Thermo Finnigan LCQ Advantage mass spectrometer.

The chromatographic purity of products was assessed using Waters Alliance 2695 separation modules with a Waters 2996 PDA detector HPLC system using a gradient of water and acetonitrile (ACN) with 0.1% trifluoroacetic acid (TFA) and thin layer chromatography (TLC) on silica gel 60 F254 (APCO, China). TLC plates were visualized by using either a UV lamp or anisaldehyde stain (by volume: 93% ethanol, 3.5% sulfuric acid, 1% acetic acid and 2.5% anisaldehyde). Chromatographic separations were performed using silica gel (APCO, China; 300-400 µm mesh size).

All chemicals were obtained from commercial sources and used as received unless otherwise stated. All experiments were conducted under an atmosphere of dry argon. Only the 20(S)-camptothecin derivative was used in all the experiments.

2. Preparation of S,R-topotecan lactate

2.1. (R)-(+)-Methyl 2-(tert-butyldimethylsilyloxy)propanoate

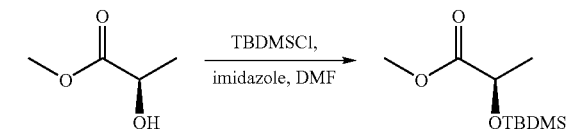

TBDMS = tert-butyldimethyl silane; DMF = dimethylformamide.

To a solution of (R)-(+)-methyl lactate (2.95 g, 28.34 mmol) in DMF (20 mL) was added tert-butyldimethyl silyl chloride (6.41 g, 42.51 mmol) and imidazole (6.75 g, 99.18 mmol). After stirring at a room temperature for 18 hr, the reaction mixture was diluted with a saturated aqueous NaCl solution (90 mL) and extracted with petroleum ether (3×60 mL). The organic layer was washed with a cold 3% HCl solution (30 mL) and a saturated aqueous NaCl solution (30 mL), dried over Na$_2$SO$_4$ and concentrated. The remaining residue was purified by silica gel (105 g) with petroleum ether (300 mL), followed by 3% ethyl acetate in petroleum ether (600 mL). The 3% ethyl acetate in the petroleum ether fractions was collected and the solvent was removed to give 5.26 g of (R)-(+)-Methyl 2-(tert-butyldimethylsilyloxy)propanoate as colorless oil (85% yield). $^1$H NMR (CDCl$_3$): δ 4.26 (q, 1H, J=6.8 Hz, —CH), 3.65 (s, 3H, —OCH$_3$), 1.32 (d, 3H, J=6.8 Hz, —CH$_3$), 0.83 (s, 9H, Si—(CH$_3$)$_3$), 0.03 (s, 3H, Si—CH$_3$), 0.00 (s, 3H, Si—CH$_3$).

2.2. (R)-(+)-2-(tert-butyldimethylsilyloxy)propanoic acid

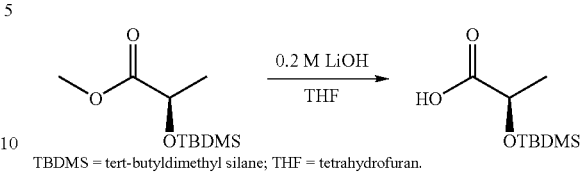

TBDMS = tert-butyldimethyl silane; THF = tetrahydrofuran.

To a solution of (R)-(+)-Methyl 2-(tert-butyldimethylsilyloxy)propanoate (5.26 g, 24.09 mmol) in THF (283 mL) at 0° C. was added an aqueous LiOH solution (0.2 M, 283 mL). After stirring at room temperature for 4 hr, the reaction mixture was concentrated to 50% of the original volume and extracted with petroleum ether (2×50 mL). The ether extracts were combined and extracted with a saturated aqueous NaHCO$_3$ solution (50 mL). The aqueous layers were combined and acidified to pH 3 to 4 with an aqueous KHSO$_4$ solution (1M, 100 mL). The aqueous solution was extracted with petroleum ether (3×250 mL) and the combined organic layers were dried over Na$_2$SO$_4$ and concentrated to afford 5.45 g of (R)-(+)-2-(tert-butyldimethylsilyloxy)propanoic acid as colorless oil (100%, product contains ~10% water). $^1$H NMR (CDCl$_3$): δ 4.29 (q, 1H, J=6.8 Hz, —CH), 1.38 (d, 3H, J=6.8 Hz, —CH$_3$), 0.86 (s, 9H, Si—(CH$_3$)$_3$), 0.07 (s, 3H, Si—CH$_3$), 0.06 (s, 3H, Si—CH$_3$).

2.3. 10-tert-butoxycarbonyloxycamptothecin (Boc-10H-CPT)

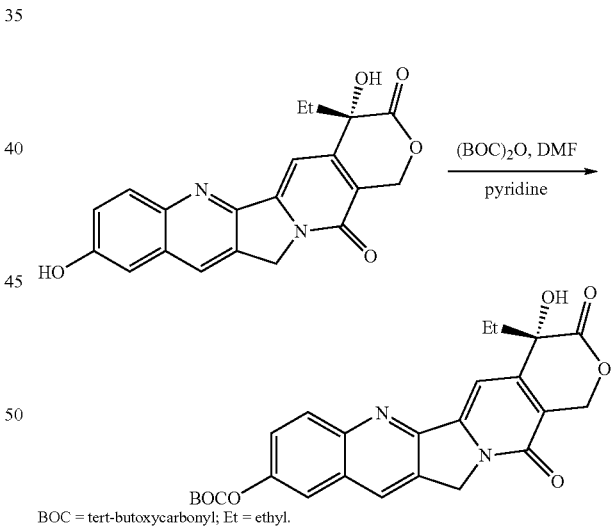

BOC = tert-butoxycarbonyl; Et = ethyl.

(BOC)$_2$O (390 g, 1.78 mol) and 10-hydroxy-camptothecin (325 g, 0.89 mol) were dissolved in DMF (4.45 L), and pyridine (1.48 L) was added. The mixture was stirred at room temperature overnight (solution is clear initially but precipitate will form gradually). The reaction mixture was diluted with DCM (2.6 L), washed with water (3×1 L) and 1 N HCl (3×1 L), and dried over Na$_2$SO$_4$. The solvent was evaporated to give 375 g of crude product, Boc-10H-CPT (90% yield). The crude product can be used right away without further purification. $^1$H NMR (CDCl$_3$): δ 8.34 (s, 1H, H7), 8.25 (s, 1H, H12), 8.21 (s, 1H, H11), 7.75 (d, 1H, J=2.4 Hz, Ar), 7.67

(s, 1H), 7.66 (dd, J=8.0, 2.4 Hz, 1H, Ar), 5.75 (d, J=16.5 Hz, 1H, —C—CH₂—O—C(O)—), 5.31 (d, J=16.5 Hz, 1H, —C—CH₂—O—C(O)—), 5.30 (s, 2H, —C—CH₂—N—), 1.91 (m, J=6 Hz, 2H, CH₂-Me), 1.62 (s, 9H, t-Bu), 1.06 (t, J=6 Hz, 3H, CH₃).

2.4. Camptothecin-10-O-tert-butoxycarbonyl-20-O—[(R)-(+)-2-(tert-butyl dimethylsilyloxy)propionate

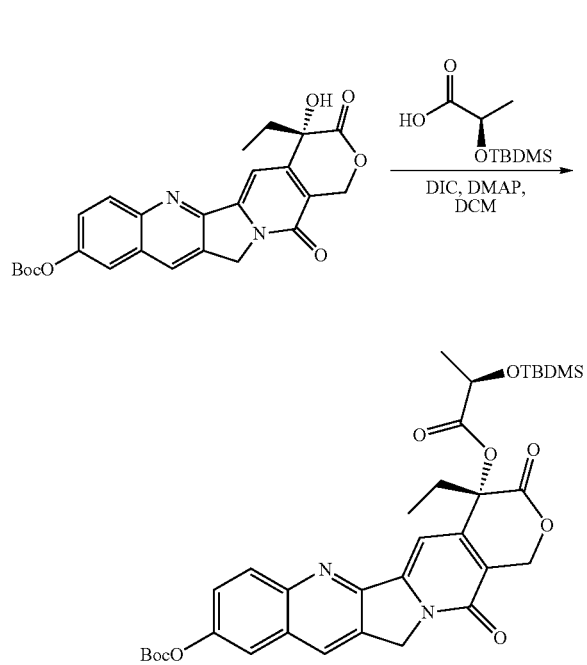

BOC = tert-butoxycarbonyl; DCM = dichloromethane; DIC = N,N′-diiopropylcarbodiimide; DMAP = 4-(dimethylamino)pyridine; TBDMS = tert-butyldimethyl silane.

To a solution of (R)-(+)-2-(tert-butyldimethylsilyloxy)propanoic acid (5.31 g, 26.03 mmol) and Boc-10H-CPT (2 g, 4.20 mmol) in CH₂Cl₂ (43 mL) was added DMAP (210 mg, 1.72 mmol) and DIC (6 mL, 38.79 mmol). The reaction was stirred at room temperature for 28 hr. The mixture was washed with 1N HCl (2×25 mL) and a saturated aqueous NaHCO₃ solution (2×25 mL), dried over Na₂SO₄ and filtered. The solvent was evaporated and the remaining residue was combined with DCM (25 mL), sonicated for a few minutes and concentrated. The remaining residue was purified by a silica gel column with 80% EtOAc:Hexanes to give 2.77 g of camptothecin-10-O-tert-butoxycarbonyl-20-O—[(R)-(+)-2-(tert-butyldimethyl silyloxy) propionate as light yellow solid (99% yield). ¹H NMR (CDCl₃): δ 8.36 (s, 1H, H7), 8.21 (d, 1H, J=9.2 Hz, H12), 7.76 (s, 1H, H9), 7.67 (d, 1H, J=9.2 Hz, H11), 7.24 (s, 1H, H14), 5.70 (d, 1H, J=17.2 Hz, H17), 5.40 (d, 1H, J=17.2 Hz, H17), 5.30 (s, 2H, H5), (q, 1H, J=6.4 Hz, —CH— lactate), 2.22 (dm, 2H, J=6.8, 44.8 Hz, —CH₂—, H19), 1.62 (s, 9H, boc), 1.48 (d, 3H, J=6.8 Hz, —CH₃, lactate), 1.02 (t, 3H, J=7.6 Hz, —CH₃, H18), 0.93 (s, 9H, Si—(CH₃)₃), 0.15 (s, 3H, Si—CH₃), 0.12 (s, 3H, Si—CH₃).

2.5. S,R-topotecan lactate

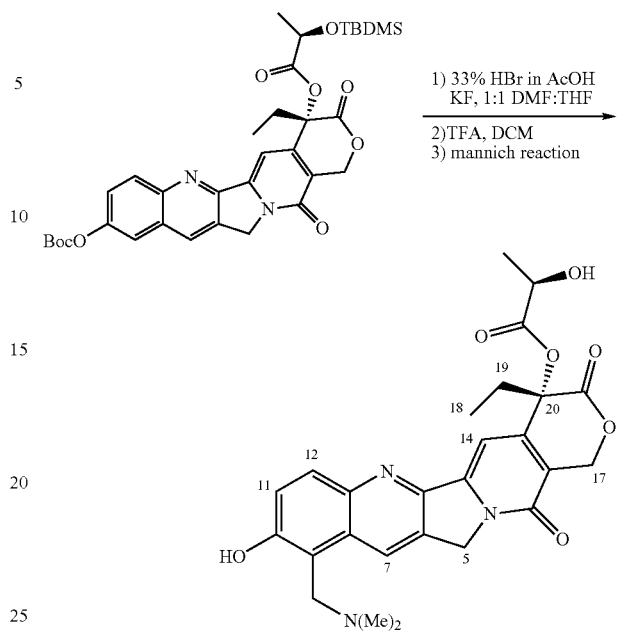

AcOH = acetic acid; BOC = tert-butoxycarbonyl; DCM = dichloromethane; DIC = N,N′-diiopropylcarbodiimide; DMAP = 4-(dimethylamino)pyridine; DMF = N,N′-dimethylformamide; Me = methyl; TBDMS = tert-butyldimethyl silane, TFA = trifluoroacetic acid, THF = tetrahydrofuran; KF = potassium floride.

To a solution of camptothecin-10-O-tert-butoxycarbonyl-20-O—[(R)-(+)-2-(tert-butyldimethylsilyloxy)propionate (2.77 g, 4.25 mmol) in 1:1 THF:DMF (48 mL) was added 33% HBr in AcOH (7.5 mL, 42.55 mmol) and KF (2 g, 34.04 mmol). The reaction was stirred at room temperature for 19 hr. The mixture was diluted with DCM (300 mL), washed with water (3×200 mL) and dried over Na₂SO₄. The solvent was evaporated and the remaining residue was dissolved in EtOAc (15 mL) and mixed with petroleum ether (10 mL). The precipitate was collected by filtration and dried to give 1.65 g of camptothecin-10-O-tert-butoxycarbonyl-20-O—[(R)-(+)-2-hydroxypropionate crude product (72% crude yield).

The crude camptothecin-10-O-tert-butoxycarbonyl-20-O—[(R)-(+)-2-hydroxypropionate (1.65 g, 3.08 mmol) was dissolved in DCM (15 mL) and mixed with TFA (4.6 mL, 61.55 mmol). After stirring at room temperature for 2 hr, bis-(dimethylamino)-methane (3.36 mL, 24.62 mmol) was added slowly. After 12 hr at room temperature, the solvent was removed and the crude was purified by reverse phase preparative HPLC using a gradient of water and acetonitrile with 0.1% trifluoroacetic acid to afford 991 mg of S,R-topotecan lactate (65% yield).

2.6. HCl Salt of S,R-topotecan lactate

S,R-topotecan lactate was converted to a HCl salt by azeotroping the TFA salt (950 mg, 1.56 mmol) with hydrogen chloride in a MeOH solution (prepared by mixing 100 mL of MeOH with 25 mL of 4M HCl in dioxane) to give 760 mg of S,R-topotecan lactate as a HCl salt (92% yield). ¹H NMR (DMSO-d6): δ 8.89 (s, 1H, H7), 8.16 (d, 1H, J=9.2 Hz, H12), 7.61 (d, 1H, J=9.2 Hz, H11), 7.00 (s, 1H, H14), 5.47 (s, 2H, H17), 5.27 (dd, 2H, J=22 Hz, —CH₂—N(Me)₂), 4.69 (s, 2H, H5), 4.40 (q, 1H, J=6.8 Hz, —CH— lactate), 2.82 (s, 6H, —N(CH₃)₂), 2.10 (q, 2H, J=8.8 Hz, —CH2—, H19), 1.32 (d, 3H, J=6.8 Hz, —CH₃ lactate), 0.91 (t, 3H, J=6.8 Hz, —CH₃, H18); IR (KBr): 3232 (OH), 1751 (lactone), 1664 (pyridone), 1598, 1508, 1298, 1251, 1202, 1132 and 1055 cm⁻¹; M.p. 212-215° C. (dec); ESIMS: calcd for C₂₆H₂₇N₃O₇ [M+H]⁺ 493.18, found 494.1.

3. Preparation of S,S-topotecan lactate

3.1. (S)-(−)-Ethyl 2-(tert-butyldimethylsilyloxy)propanoate

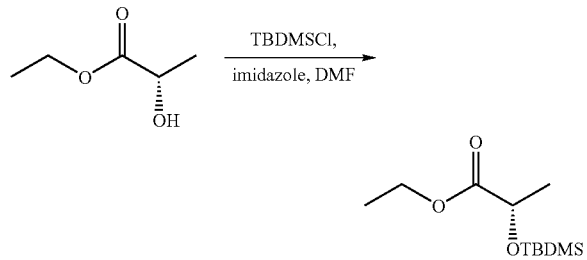

TBDMS = tert-butyldimethyl silane; DMF = dimethylformamide.

To a solution of (S)-(−)-ethyl lactate (20 mL, 191.06 mmol) in DMF (191 mL) was added tert-butyldimethyl silyl chloride (39.6 g, 262.59 mmol) and imidazole (41.6 g, 612.72 mmol). After stirring at room temperature for 20 hr, the reaction mixture was diluted with a saturated aqueous NaCl solution (600 mL) and extracted with petroleum ether (3×400 mL). The organic layer was washed with a cold 3% HCl solution (200 mL) and a saturated aqueous NaCl solution (200 mL), dried over $Na_2SO_4$ and concentrated. The remaining residue was purified by silica gel (700 g) with petroleum ether (2 L), followed by 3% ethyl acetate in petroleum ether (4 L). The 3% ethyl acetate in the petroleum ether fractions was collected and the solvent was removed to give 36.57 g of (S)-(−)-ethyl 2-(tert-butyldimethylsilyloxy)propanoate as colorless oil (82% yield). $^1$H NMR ($CDCl_3$): δ 4.23 (q, 1H, J=6.8 Hz, H2, —CH—), 4.11 (q, 2H, J=7.2 Hz, —$CH_2$—), 1.32 (d, 3H, J=6.8 Hz, H3, —$CH_3$), 1.21 (t, 3H, J=7.2 Hz, —$CH_3$), 0.83 (s, 9H, Si—$(CH_3)_3$), 0.03 (s, 3H, Si—$CH_3$), 0.00 (s, 3H, Si—$CH_3$).

3.2. (S)-(−)-2-(tert-butyldimethylsilyloxy)propanoic acid

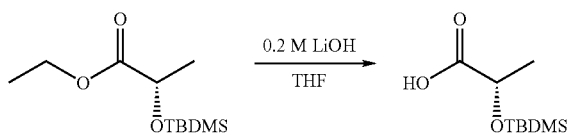

TBDMS = tert-butyldimethyl silane; THF = tetrahydrofuran

To a solution of (S)-(−)-ethyl 2-(tert-butyldimethylsilyloxy)propanoate (10.0 g, 43.04 mmol) in THF (430 mL) at 0° C. was added an aqueous LiOH solution (0.2 M, 430 mL). After stirring at room temperature for 5 hr, the reaction mixture was concentrated to 50% of the original volume and extracted with petroleum ether (2×80 mL). The ether extracts were combined and extracted with a saturated aqueous $NaHCO_3$ solution (80 mL). The aqueous layers were combined and acidified to pH 3 to 4 with an aqueous $KHSO_4$ solution (1 M, 175 mL). The aqueous solution was extracted with petroleum ether (3×300 mL) and the combined organic layers were dried over $Na_2SO_4$ and concentrated to afford 6.96 g of (S)-(−)-2-(tert-butyldimethylsilyloxy)propanoic acid as colorless oil (79% yield). $^1$H NMR ($CDCl_3$): δ 4.26 (q, 1H, J=6.8 Hz, —CH), 1.35 (d, 3H, J=6.8 Hz, —$CH_3$), 0.82 (s, 9H, Si—$(CH_3)_3$), 0.03 (s, 3H, Si—$CH_3$), 0.02 (s, 3H, Si—$CH_3$).

3.3. Camptothecin-10-O-tert-butoxycarbonyl-20-O—[(S)-(−)-2-(tert-butyldimethylsilyloxy)propionate

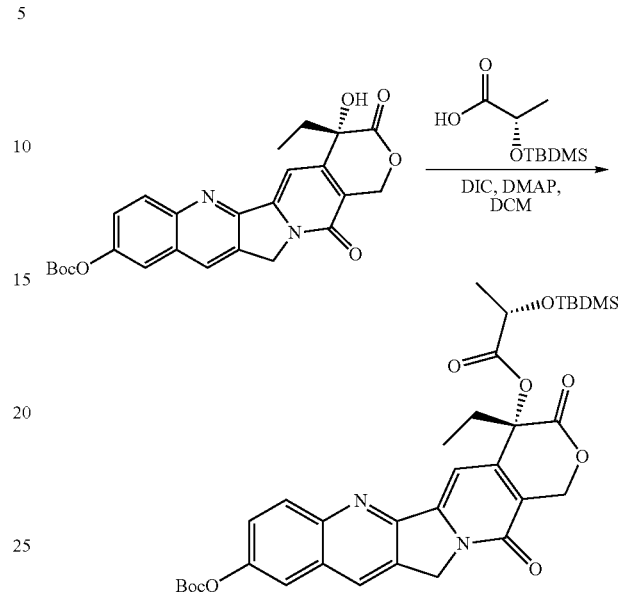

BOC = tert-butoxycarbonyl; DCM = dichloromethane; DIC = N,N'-diiopropylcarbodiimide; DMAP = 4-(dimethylamino)pyridine; TBDMS = tert-butyldimethyl silane.

To a solution of (S)-(−)-2-(tert-butyldimethylsilyloxy)propanoic acid (5.33 g, 26.11 mmol) and Boc-10H-CPT (2 g, 4.30 mmol) in $CH_2Cl_2$ (43 mL) was added DMAP (210 mg, 1.72 mmol) and DIC (6 mL, 38.79 mmol). The reaction was stirred at room temperature for 28 hr. The mixture was washed with 1N HCl (2×25 mL) and a saturated aqueous $NaHCO_3$ solution (2×25 mL), dried over $Na_2SO_4$ and filtered. The solvent was evaporated and the remaining residue was combined with DCM (25 mL), sonicated for a few minutes and concentrated. The remaining residue was purified by a silica gel column with 80% EtOAc:Hexanes to give 1.27 g of camptothecin-10-O-tert-butoxycarbonyl-20-O—[(S)-(−)-2-(tert-butyldimethylsilyloxy) propionate as light yellow solid (45% yield). $^1$H NMR ($CDCl_3$): δ 8.36 (s, 1H, H7), 8.21 (d, 1H, J=9.2 Hz, H12), 7.76 (s, 1H, H9), 7.67 (d, 1H, J=9.2 Hz, H11), 7.24 (s, 1H, H14), 5.70 (d, 1H, J=17.2 Hz, H17), 5.40 (d, 1H, J=17.2 Hz, H17), 5.30 (s, 2H, H5), (q, 1H, J=6.4 Hz, —CH— lactate), 2.22 (dm, 2H, J=6.8, 44.8 Hz, —CH2-, H19), 1.62 (s, 9H, boc), 1.48 (d, 3H, J=6.8 Hz, —$CH_3$, lactate), 1.02 (t, 3H, J=7.6 Hz, —$CH_3$, H18), 0.93 (s, 9H, Si—$(CH_3)_3$), 0.15 (s, 3H, Si—$CH_3$), 0.12 (s, 3H, Si—$CH_3$).

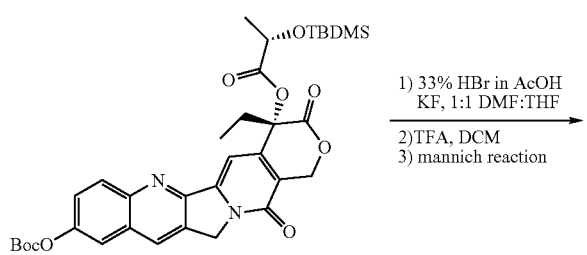

-continued

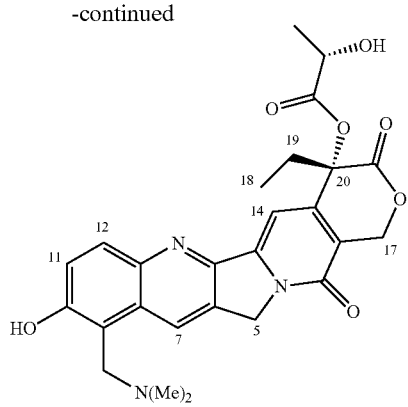

AcOH = acetic acid; BOC = tert-butoxycarbonyl; DCM = dichloromethane; DIC = N,N'-diiopropylcarbodiimide; DMAP = 4-(dimethylamino)pyridine; DMF = N,N'-dimethylformamide; Me = methyl; TBDMS = tert-butyldimethyl silane, TFA = trifluoroacetic acid, THF = tetrahydrofuran.

3.4. S,S-topotecan lactate

To a solution of camptothecin-10-O-tert-butoxycarbonyl-20-O—[(S)-(−)-2-(tert-butyldimethylsilyloxy)propionate (1.27 g, 1.95 mmol) in 1:1 THF:DMF (22 mL) was added 33% HBr in AcOH (3.42 mL, 19.51 mmol) and KF (910 mg, 15.61 mmol). The reaction was stirred at room temperature for 19 hr. The mixture was diluted with DCM (150 mL), washed with water (3×100 mL) and dried over $Na_2SO_4$. The solvent was evaporated and the remaining residue was dissolved in EtOAc (12 mL) and added petroleum ether (50 mL). The precipitate was collected by filtration and dried to give 860 mg of camptothecin-10-O-tert-butoxycarbonyl-20-O—[(S)-(−)-2-hydroxypropionate crude product (82% crude yield).

The crude camptothecin-10-O-tert-butoxycarbonyl-20-O—[(S)-(+2-hydroxypropionate (860 mg, 1.60 mmol) was dissolved in DCM (8 mL) and added TFA (2.38 mL, 32.08 mmol). After stirring at room temperature for 2 hr, bis-(dimethylamino)-methane (1.75 mL, 12.83 mmol) was added slowly. After 12 hr at room temperature, the solvent was removed and the crude was purified by reverse phase preparative HPLC using a gradient of water and acetonitrile with 0.1% trifluoroacetic acid to afford 525 mg of S,S-topotecan lactate (66% yield).

3.5. HCl Salt of S,S-topotecan lactate

S,S-topotecan lactate was converted to a HCl salt by azeotroping the TFA salt (450 mg, 0.74 mmol) with hydrogen chloride in a MeOH solution (prepared by mixing 40 mL of MeOH with 10 mL of 4M HCl in dioxane) to give 380 mg of S,S-topotecan lactate as a HCl salt (97% yield). $^1H$ NMR (DMSO-d6): δ 8.89 (s, 1H, H7), 8.16 (d, 1H, J=9.2 Hz, H12), 7.61 (d, 1H, J=9.2 Hz, H11), 7.00 (s, 1H, H14), 5.47 (s, 2H, H17), 5.27 (dd, 2H, J=22 Hz, —$CH_2$—$N(Me)_2$), 4.69 (s, 2H, H5), 4.40 (q, 1H, J=6.8 Hz, —CH— lactate), 2.82 (s, 6H, —$N(CH_3)_2$), 2.10 (q, 2H, J=8.8 Hz, —CH2-, H19), 1.32 (d, 3H, J=6.8 Hz, —$CH_3$ lactate), 0.91 (t, 3H, J=6.8 Hz, —$CH_3$, H18); IR (KBr): 3232 (OH), 1751 (lactone), 1664 (pyridone), 1598, 1508, 1298, 1251, 1202, 1132 and 1055 $cm^{-1}$; M.p. 212-215° C. (dec); ESIMS: calcd for $C_{26}H_{27}N_3O_7$ $[M+H]^+$ 493.18, found 494.1.

EXAMPLE 4

HPLC Comparison

To confirm the chemical structures of U1 and U2, a HPLC comparison analysis was performed. Briefly, the rat blood samples (containing U1 and U2) obtained according to Example 1 and the synthetic topotecan lactates (S,R and S, S) obtained according to Example 4 were injected into a Waters HPLC system (Waters 2695) which was equipped with a Gemini® reverse phase column (35° C.) and an UV detection unit (Waters 2996) and run under the condition of 50 mM phosphate buffer (pH 4.0)/methanol as mobile phase (1.0 mL/min flow rate). The gradient elution program is shown in Table 3.

TABLE 3

Gradient elution program

| Time | % Buffer | % MeOH |
| --- | --- | --- |
| 0.01 | 80 | 20 |
| 5 | 40 | 60 |
| 20 | 20 | 80 |
| 21 | 10 | 90 |
| 23 | 10 | 90 |
| 25 | 80 | 20 |
| 30 | 80 | 20 |

The eluted products were detected at 254 nm. According to the comparative chromatograms thus obtained (data not shown), the peak of the synthetic S,R-topotecan lactate at the retention time of 7.436 min exactly matches the peak of U1 from the rat blood samples; and the peak of the synthetic S,S-topotecan lactate at the retention time of 7.700 min exactly matches the peak of U2 from the rat blood samples. Therefore, U1 was confirmed as S,R-topotecan lactate, and U2 was confirmed as S,S-topotecan lactate.

EXAMPLE 5

In Vitro Cytotoxicity Assay

1. Cell Culture

Five tumor cell lines, HCT-116 (obtained from Dr. Yang's lab, Dr. Li-Xi Yang-Radiobiology Laboratory, California Pacific Medical Center Research Institute, San Francisco, Calif.), HT-29 (available from American Type Culture Collection, ATCC), MCF-7 (available from ATCC), DMS-114 (obtained from Dr. Yang's lab, supra) and PC14PE6/AS2 (obtained from Dr. Su W C, National Cheng Kung University), were provided and cultured according to the instructions provided by ATCC.

Briefly, HCT-116 was cultured in McCoy's 5a medium (Sigma-Aldrich, St Louis, Mo., USA) with fetal bovine serum (10%, v/v) (Hyclone Laboratories, Logan, Utah), L-glutamine (Invitrogen, Carlsbad, Calif.), sodium pyruvate (Hyclone Laboratories, Logan, Utah), penicillin and streptomycin (Invitrogen, Carlsbad, Calif.). HT-29 was cultured in RPMI-1640 medium (Hyclone Laboratories, Logan, Utah) with fetal bovine serum (10%, v/v) (Hyclone Laboratories, Logan, Utah), L-glutamine (Invitrogen, Carlsbad, Calif.), sodium pyruvate (Hyclone Laboratories, Logan, Utah), penicillin and streptomycin (Invitrogen, Carlsbad, Calif.). MCF7 was cultured in DMEM medium (Hyclone Laboratories, Logan, Utah) with fetal bovine serum (10%, v/v) (Hyclone Laboratories, Logan, Utah), L-glutamine (Invitrogen, Carlsbad, Calif.), sodium pyruvate (Hyclone Laboratories, Logan, Utah), penicillin and streptomycin (Invitrogen, Carlsbad, Calif.). DMS-114 was cultured in RPMI-1640 medium with fetal bovine serum (10%, v/v) at 37, 5% $CO_2$. PC14PE6/AS2 was cultured in MEMα medium (Hyclone Laboratories, Logan, Utah) with fetal bovine serum (10%, v/v) (Hyclone Laboratories, Logan, Utah), L-glutamine (Invitrogen, Carlsbad, Calif.), sodium pyruvate (Hyclone Laboratories, Logan, Utah), penicillin and streptomycin (Invitrogen, Carlsbad, Calif.) as well as addition of 1% MEM vitamin solution (Invitrogen, Carlsbad, Calif.).

2. IC$_{50}$ Measurement

Synthetic S,R-topotecan lactate (U1) was dissolved in 100% dimethyl sulfoxide (DMSO) to obtain a U1 stock solution (2 mM). The U1 stock solution was then 20-fold diluted with 5 mM citric acid, and serial diluted with 5 mM citric acid and 5% DMSO to obtain U1 solutions of various concentrations from 1 mM to 0.015 µM. U2 solutions of various concentrations were prepared in the same way. 2-(2,4,5,7-tetranitro-9-fluorenylideneaminooxy)propionic acid (TAPA) of the following structure was used as a reference compound.

TAPA

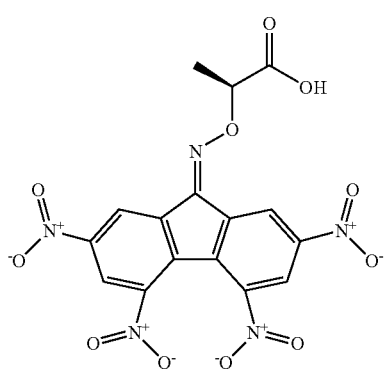

TAPA was first dissolved in 100% DMSO to obtain a TAPA stock solution (20 mM). The TAPA stock solution was then sixty-six (66)-fold diluted with 9% DMSO and 90% ACN in 5 mM citric acid, and serial diluted to obtain TAPA solutions of various concentrations from 0.3 mM to 0.0045 µM.

$4\times10^3$ to $1\times10^4$ cells suspended in 100 µL culture medium were plated in each well of 96-well plates and incubated overnight. To the cell cultures, proper amounts of the above-mentioned compound solutions (U1, U2, or TAPA) were added so that the cells were incubated with different concentrations of the compound (U1, U2 or TAPA) from about $1\times10^{-4}$ to $1\times10^1$ µM. After 72 hours of incubation, cells were fixed by gently adding 50 µL of cold 50% (w/v) trichloroethane (TCA, Sigma, St Louis, Mo., USA; 10% TCA as final concentration) and incubating for 60 minutes at 4° C. The supernatants were discarded, and the plates were washed five times with tap water and air-dried. 100 µL of sulforhodamine B (SRB, Sigma, St. Louis, Mo., USA) in a concentration of 0.4% (w/v) in 1% acetic acid (Fluka, Seelze, Germany) was subsequently added to each well and incubated at room temperature for 10 minutes. After staining, unbound dye was removed by washing five times with 1% acetic acid and the plates were again air-dried. Bound stain in each well was dissolved with 10 mM trizma base (Bioshop, Burlington, ON, Canada), and the absorbance was measured at 515 nm using an automated plate reader (Anthos 2001, Anthos Labtec Instrument). IC$_{50}$ values were determined based on the absorbance thus measured and shown in Table 4.

TABLE 4

| Cell lines | Test compounds | IC$_{50}$ (µM) |
|---|---|---|
| HCT-116 | S,S-topotecan lactate (U2) | 0.045 |
| (Human colon cancer) | S,R-topotecan lactate (U1) | 0.058 |
| | TAPA | >10 |
| HT-29 | S,S-topotecan lactate (U2) | 0.056 |

TABLE 4-continued

| Cell lines | Test compounds | IC$_{50}$ (µM) |
|---|---|---|
| (Human colon cancer) | S,R-topotecan lactate (U1) | 0.056 |
| | TAPA | ND* |
| MCF-7 | S,S-topotecan lactate (U2) | 0.143 |
| (Human breast cancer) | S,R-topotecan lactate (U1) | 0.194 |
| | TAPA | 6.19 |
| DMS-114 | S,S-topotecan lactate (U2) | 0.026 |
| (Small cell lung cancer) | S,R-topotecan lactate (U1) | 0.053 |
| | TAPA | 0.925 |
| PC14PE6/AS2 | S,S-topotecan lactate (U2) | 0.074 |
| (Non-small cell lung cancer) | S,R-topotecan lactate (U1) | 0.021 |
| | TAPA | 3.33 |

*ND: Not determined

As shown in Table 4, the compounds of the invention (U1 and U2) exhibited inhibitory effects on growth of various cancer cells.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A compound which is represented by Formula I

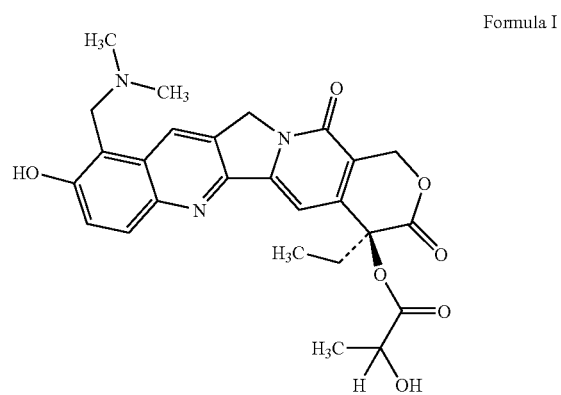

Formula I or a pharmaceutically acceptable salt thereof.

2. The compound of claim 1, which is represented by Formula II

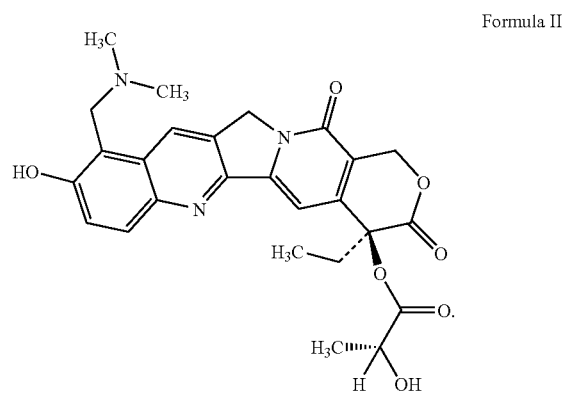

Formula II

3. The compound of claim 1, which is represented by Formula III

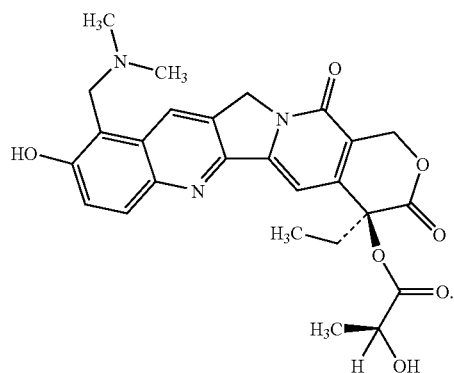

Formula III

4. A pharmaceutical composition comprising a compound according to claim 1 or a pharmaceutically acceptable salt thereof together with a pharmaceutically acceptable carrier.

5. A pharmaceutical composition comprising a compound according to claim 2 or a pharmaceutically acceptable salt thereof together with a pharmaceutically acceptable carrier.

6. A pharmaceutical composition comprising a compound according to claim 3 or a pharmaceutically acceptable salt thereof together with a pharmaceutically acceptable carrier.

* * * * *